(12) United States Patent
Hines

(10) Patent No.: US 6,274,294 B1
(45) Date of Patent: Aug. 14, 2001

(54) CYLINDRICAL PHOTOLITHOGRAPHY EXPOSURE PROCESS AND APPARATUS

(75) Inventor: Richard A. Hines, Stilwell, KS (US)

(73) Assignee: Electroformed Stents, Inc., Stilwell, KS (US)

( * ) Notice: Subject to any disclaimer, the term of this patent is extended or adjusted under 35 U.S.C. 154(b) by 0 days.

(21) Appl. No.: 09/243,252

(22) Filed: Feb. 3, 1999

(51) Int. Cl.[7] .................................................. G03F 7/04
(52) U.S. Cl. .............................................................. 430/322
(58) Field of Search .................................. 430/322, 308; 263/1

(56) References Cited

U.S. PATENT DOCUMENTS

| | | |
|---|---|---|
| 4,343,048 | 8/1982 | Ross et al. . |
| 4,434,547 * | 3/1984 | Pascal et al. ............................ 29/599 |
| 4,509,426 * | 4/1985 | Hardin ................................ 101/348 |
| 4,733,665 | 3/1988 | Palmaz . |
| 4,776,337 | 10/1988 | Palmaz . |
| 4,944,087 * | 7/1990 | Landi ..................................... 29/848 |
| 5,102,417 | 4/1992 | Palmaz . |
| 5,195,984 | 3/1993 | Schatz . |
| 5,366,504 | 11/1994 | Andersen et al. . |
| 5,421,955 | 6/1995 | Lau et al. . |
| 5,443,498 | 8/1995 | Fontaine . |
| 5,443,500 | 8/1995 | Sigwart . |
| 5,449,373 | 9/1995 | Pinchasik et al. . |
| 5,464,419 | 11/1995 | Glastra . |
| 5,649,952 | 7/1997 | Lam . |
| 5,741,429 | 4/1998 | Donadio, III et al. . |
| 6,019,784 * | 2/2000 | Hines ....................................... 623/1 |

OTHER PUBLICATIONS

Trolier–McKinstry et al., "Optical Fibers with Patterned ZnO/Electrode Coatings for Flexural Actuators," 459 Mat. Res. Soc. Symp. Proc., pp. 189–195 (1997).

Winslow, Ron, "J&J's 'Stent' is Changing Coronary Care," *The Wall Street Journal*, Oct. 23, 1995, pp. A1, A8.

Benko, Laura B., "Keeping the Flow Going for Heart Patients," *Investor's Business Daily*, May 24, 1996, p. A4.

Waite, Thomas E., "Stent, Stents, Stents," *Investor's News Wire*, Nov. 18, 1996.

* cited by examiner

*Primary Examiner*—Shean C. Wu
(74) *Attorney, Agent, or Firm*—Hovey, Williams, Timmons & Collins

(57) ABSTRACT

The present invention is directed to a novel apparatus for exposing a pattern onto a photoresist-coated substrate cylinder and the process of using the apparatus. The cylindrical photolithography apparatus of the present invention comprises two adjacent cylindrical support rollers between which a portion of a flexible photomask extends in the form of a loop. The photoresist-coated substrate cylinder is received in the loop and a tension device, such as a weight, is engaged with the photomask to pull the photomask into contact with the photoresist-coated substrate cylinder over a substantial portion of the circumference of the substrate cylinder. A drive mechanism pulls the photomask over the surface of the photoresist-coated substrate cylinder thereby causing the substrate cylinder to rotate. Exposure light is provided during movement of the photomask to expose a pattern contained on the photomask onto the photoresist. In an alternative embodiment of the present invention, designed for small substrate cylinders and/or substrate cylinders coated with a thick resist, a cylindrical lens is supported above the support cylinders and the photoresist-coated substrate cylinder to focus the light from the light device in a radial direction to increase resolution of the pattern. In applications requiring even higher resolution, a panel defining an aperture slit is placed between the light device and cylindrical lens to further focus the light rays.

22 Claims, 5 Drawing Sheets

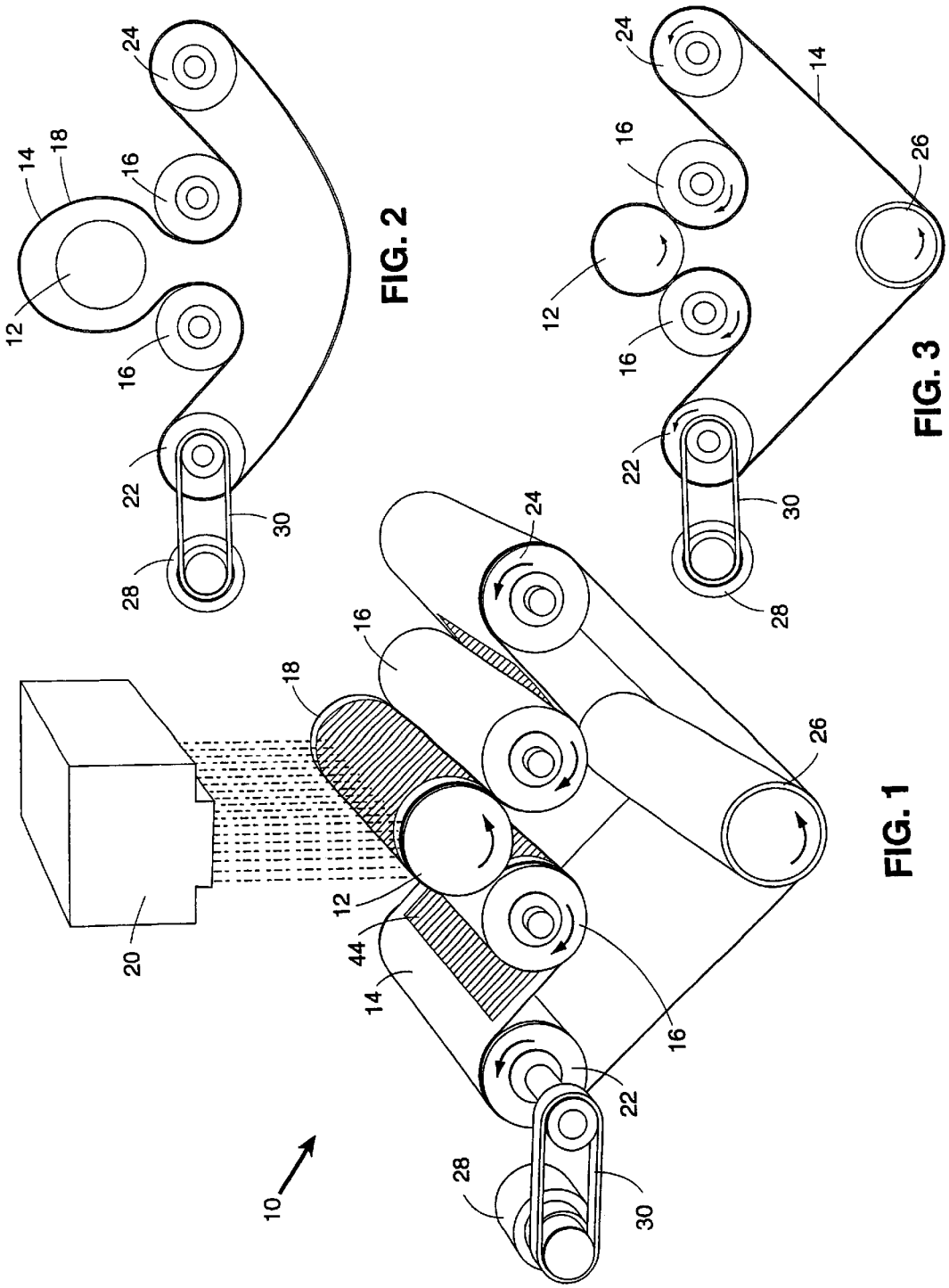

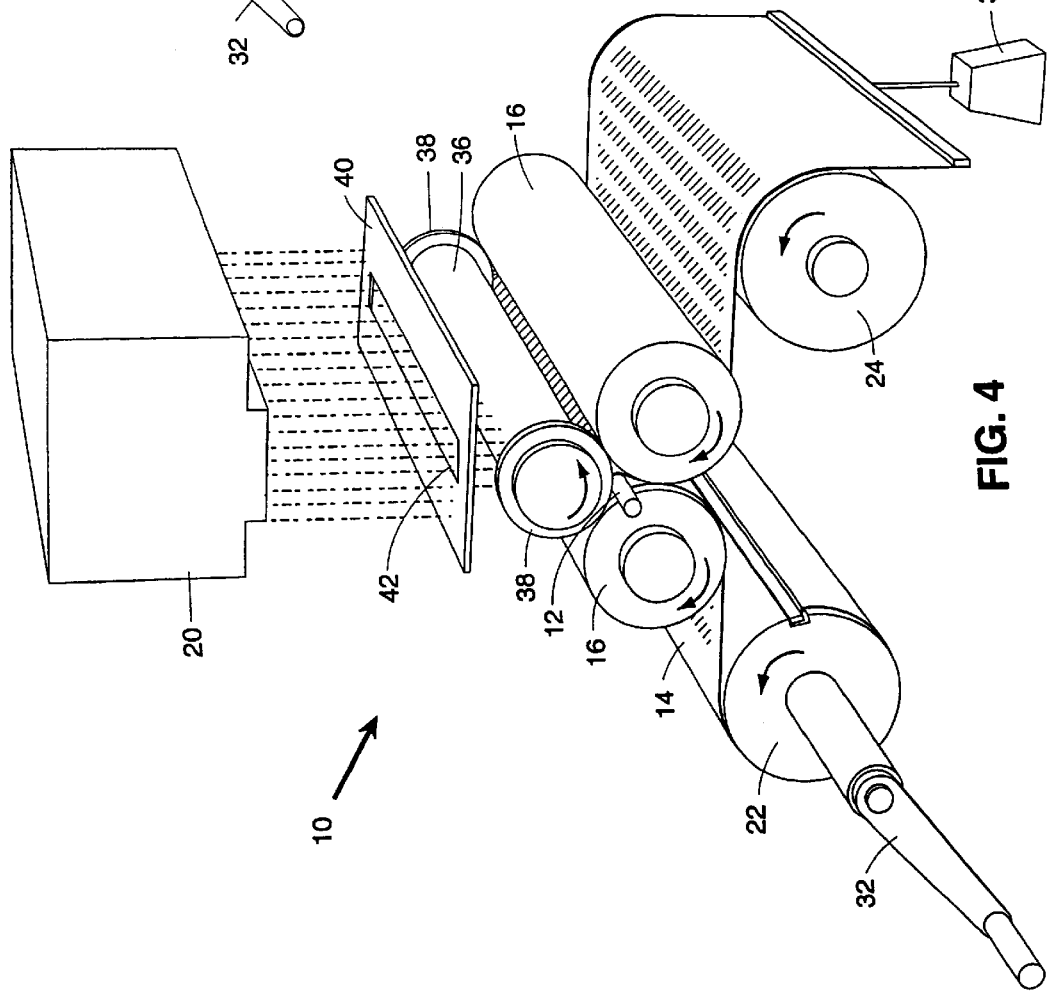
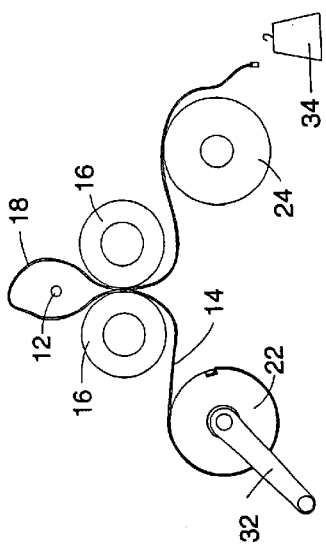
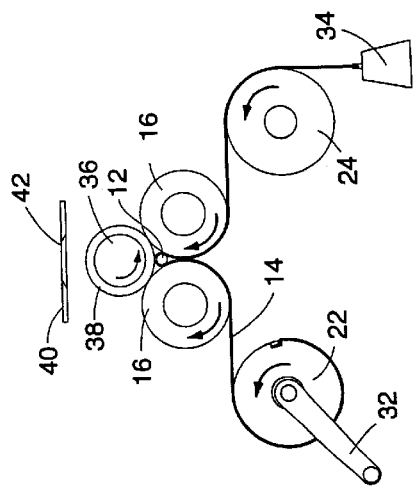

CYLINDRICAL PHOTOLITHOGRAPHY EXPOSURE PROCESS AND APPARATUS

BACKGROUND

The present invention is directed to the field of photolithography. Specifically, the present invention is directed to a novel apparatus for exposing a pattern onto a photoresist-coated substrate cylinder and the process of using the apparatus.

In the art of photolithography, an image contained on a photomask is transferred to a photoresist-coated substrate. The photoresist (also referred to simply as "resist") is sensitive to light of a specific wavelength such that when light of the appropriate wavelength passes through the transparent areas on the photomask and strikes the photoresist, the photoresist is chemically changed. Developing of the exposed photoresist removes portions of the photoresist from the substrate corresponding to the exposed or unexposed portions of the photoresist, depending on the type of photoresist used.

The image thus formed in the resist may be utilized in a number of ways. In certain applications, the resist pattern is used as a mask, protecting the substrate from an etching solution that dissolves the non-coated portion of the substrate. In other applications the resist can serve as a "mold," wherein metal is electroformed into the cavities from which the resist has been removed. In yet other applications the patterned resist is used directly to transfer ink from one surface to another as part of a printing process.

Conventional photolithography utilizes a flat photomask to transfer an image to a flat photoresist-covered substrate, wherein the :flat photomask and flat substrate are positioned in parallel planes. Collimated light perpendicular to the photomask and substrate is passed through the flat photomask to expose areas on the substrate corresponding to transparent areas of the photomask without undercutting the opaque areas of the photomask.

Conventional photolithography is not readily adaptable to curved or cylindrical substrates (also referred to herein as "substrate cylinders"). When a curved or cylindrical substrate is used with a flat photomask, the collimated light striking the substrate cylinder is perpendicular to only a narrow line on the surface of the substrate cylinder. The remainder of the substrate cylinder is exposed to nonperpendicular, or sloping, light. The nonperpendicular light results in decreased resolution of the exposed pattern, due in part to the nonperpendicular rays undercutting the opaque portion of the photomask.

Various attempts have been made to modify conventional photolithography tools and methods to expose the photomask image onto a curved or cylindrical substrate without a decrease in pattern resolution. One such method provides a narrow band of exposure light to prevent exposure of areas of the substrate cylinder removed from the line at which the light is perpendicular to the substrate cylinder. The substrate cylinder is rotated under the flat photomask as the photomask moves horizontally so as to expose the entire circumference of the substrate cylinder. Although a very narrow slit will minimize distortion from sloped light, such slits allow exposure of only a small portion of the circumference of the substrate cylinder at any one point in time, thereby significantly increasing the time required to expose the entire circumference of the substrate cylinder. In addition, it is difficult to match or align the pattern at the beginning and end of the pattern (referred to herein as the 0 and 360 degree positions). Further, it is difficult to maintain the alignment between the narrow band of light and the longitudinal axis of the substrate cylinder and, therefore, some distortion of the image is generated from such operations.

Another known method for exposing a pattern onto photoresist-coated substrate cylinders utilizes a variation of conventional contact photolithography. Contact photolithography involves direct contact between the photomask and the resist-coated substrate, which minimizes the area for exposure light to undercut the photomask and thereby provides high pattern resolution. In conventional contact photolithography, both the photomask and substrate are flat. In the variation of contact photolithography developed for exposing a pattern onto cylinders, the photomask is formed as a cylindrical sleeve having an inside diameter slightly larger than the outside diameter of the resist-coated substrate cylinder. This arrangement leaves small gaps between the photomask sleeve and substrate cylinder, which allows some undercutting of the photomask by the exposure light, thereby reducing pattern resolution. Additionally, photomask sleeves are problematic in that the soft-baked resist that is coated onto the substrate cylinder generally remains somewhat tacky, making it difficult to slide a close-fitting photomask sleeve over the substrate cylinder. It is preferable to fabricate such a photomask sleeve with the photomask image on the interior of the sleeve, so that the photomask image will be in contact with the exterior of the cylindrical substrate to minimize undercutting of the photomask. However, it is difficult to fabricate a photomask sleeve wherein the photomask image is on the interior surface of the sleeve.

Conventional photolithography is particularly unsuited to exposing patterns onto substrate cylinders of a very small diameter, such as those used to produce cardiovascular stents, because the results of undercutting are especially evident in substrate cylinders of a small diameter. The prior attempts to adapt photolithography to cylindrical substrates are not readily adaptable to substrate cylinders of a very small diameter. As a result, non-photolithographic processes for forming patterns on small substrate cylinders have also been attempted. In one such process, a resist pattern is formed on a substrate cylinder using a computer-controlled machine and laser to remove the unwanted resist. This process also is problematic in that the laser leaves rough edges that cannot be tolerated in many applications, for example, in cardiovascular stents.

Such difficulties are discussed more fully in co-pending U.S. Pat. application Ser. No. 08\819,757 now U.S. Pat. No. 6,019,784 for Electroformed Stents and co-pending U.S. Pat. application Ser. No. 09\201,972 for Uniform which applications were filed by the inventor of the present application. In these applications, the inventor discusses the benefits of using photolithography to from a resist pattern on a mandrel used for electroforming coronary stents. Coronary stents have a small diameter, generally about 0.06 inches and must have smooth edges so as not to damage the interior of the artery, or other vessel, into which they are inserted. Further, the inventor's preferred stent pattern involves an intricate series of loops and bands. Such small and/or intricate pattern should be produced with a high resolution.

Thus, while procedures for exposing a pattern in a resist-coated substrate cylinder are known, a need remains for an efficient method for exposing a continuous, high-resolution pattern around the entire circumference of a photoresist-coated substrate cylinder, including a substrate cylinder of a very small diameter.

SUMMARY OF THE INVENTION

Thus, one object of the present invention is to provide an cylindrical photolithography apparatus for exposing a high resolution pattern onto a photoresist-covered substrate cylinder.

A further object of the present invention is to provide a cylindrical photolithography apparatus that allows precise pattern overlay at the 0 and 360 degree positions of the substrate cylinder.

It is a further object of the present invention to provide a cylindrical photolithography apparatus that can accommodate a range of substrate cylinder diameters and lengths and a variety of two-dimensional patterns to be imaged onto the substrate cylinders.

It is yet another object of the present invention to provide a cylindrical photolithography apparatus that allows efficient exposure times.

The present invention is directed to a cylindrical photolithography apparatus used to expose a continuous high resolution pattern contained on a flexible photomask onto the photoresist-coated surface of a substrate cylinder. The cylindrical photolithography apparatus of the present invention utilizes and/or comprises a flexible photomask, a portion of which extends between two adjacent cylindrical support rollers so as to form a loop configured to receive the substrate cylinder. The photoresist-coated substrate cylinder is held in the loop, such that the photomask is in contact with the surface of the photoresist-coated substrate cylinder over a substantial portion of the circumference of the substrate cylinder.

The cylindrical photolithography apparatus includes a tension device for placing tension on the photomask to pull the photomask against the surface of the substrate cylinder. The cylindrical exposure apparatus also comprises a drive mechanism for driving the photomask through the apparatus and thereby driving the support rollers and substrate cylinder. Further, at least one underpinning is provided on which elements of the apparatus are mounted. An exposure light device may be provided as part of the apparatus to supply light of the appropriate wavelength to expose the photoresist.

For small diameter substrate cylinders, or substrate cylinders with a resist thickness similar to the smallest feature to be patterned, the cylindrical exposure apparatus further comprises a lens that focuses the light from the light device to strike the photoresist coating the substrate cylinder in a radial direction (i.e. along a radial line from the longitudinal axis of the substrate cylinder). Radial light will produce generally straight sidewalls on the patterned photoresist and will not undercut the photomask. In applications in which extremely high resolution is required, a panel containing a slit aperture is placed between the light device and the lens to further focus the light rays. In other applications, the panel containing the slit aperture may be used without a lens to provide sufficient resolution.

BRIEF DESCRIPTION OF THE DRAWINGS

FIG. 1 is a perspective view of the cylindrical photolithography apparatus of the present invention configured for large substrate cylinders.

FIG. 2 is a partial side elevational view of the cylindrical photolithography apparatus configured for large substrate cylinders wherein the photomask is untensioned.

FIG. 3 is a partial side elevational view of the cylindrical photolithography apparatus of the present invention configured for large substrate cylinders wherein the photomask is tensioned.

FIG. 4 is a perspective view of the cylindrical photolithography apparatus of the present invention configured for small substrate cylinders.

FIG. 5 is a partial side elevational view of the cylindrical photolithography apparatus configured for small substrate cylinders wherein the photomask is untensioned.

FIG. 6 is a partial side elevational view of the cylindrical photolithography apparatus of the present invention configured for small substrate cylinders wherein the photomask is tensioned.

DETAILED DESCRIPTION AND PREFERRED EMBODIMENTS

Figure 7:
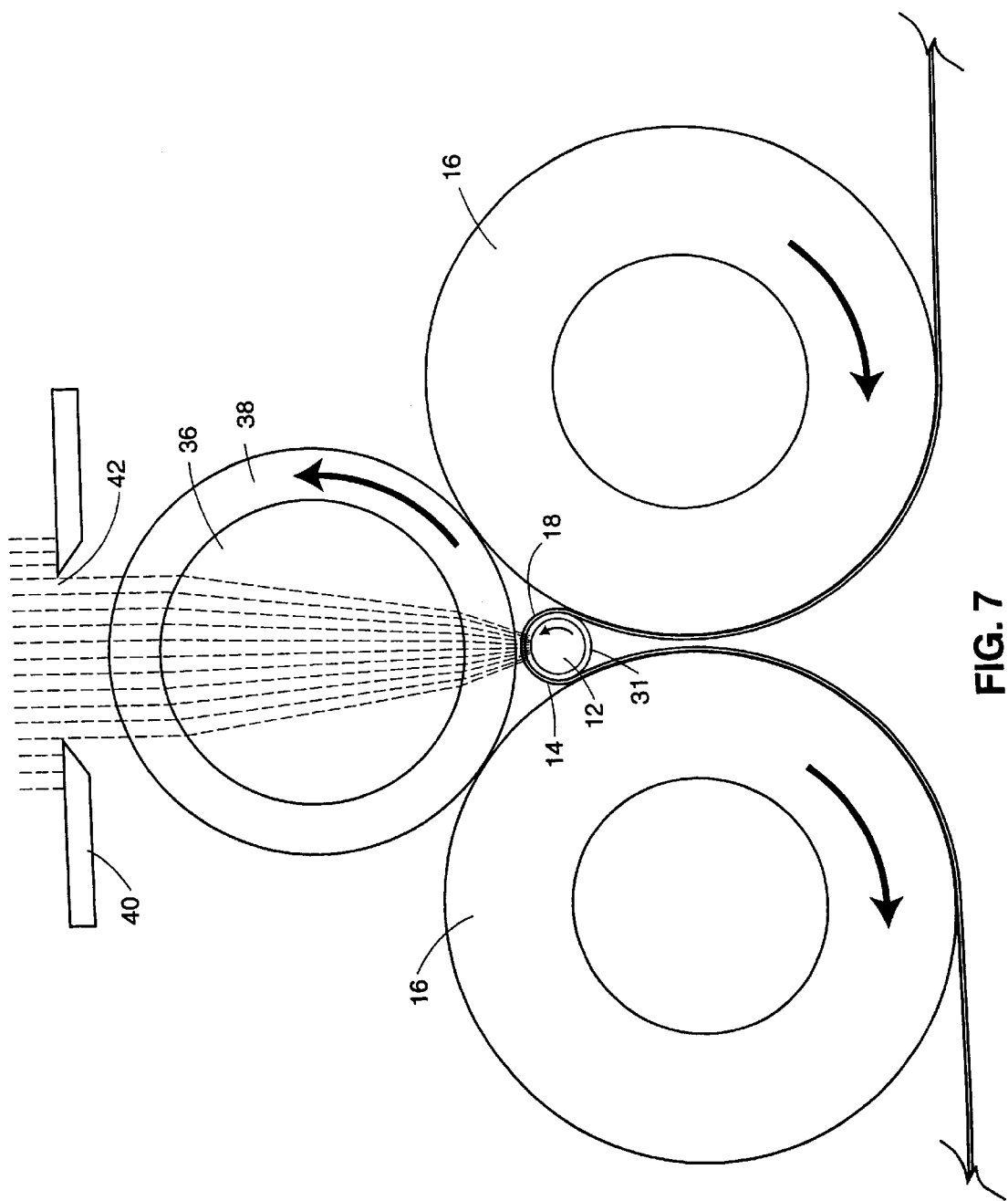
FIG. 7 is a partial side view of the cylindrical photolithography apparatus configured for small substrate cylinders showing details of a lens and slit arrangement.

Referring first to FIG. 1, the present invention is directed to a cylindrical photolithography apparatus, generally indicated by the numeral 10, that utilizes contact photolithography to expose a high resolution image onto the photoresist-coated surface of a substrate cylinder 12. The cylindrical photolithography apparatus 10 utilizes and/or comprises a flexible photomask 14, containing the pattern to be exposed, and two adjacent parallel cylindrical support rollers 16, wherein a portion of the flexible photomask 14 extends between support rollers 16 so as to form a loop 18 configured to receive substrate cylinder 12. The photoresist-coated coated substrate cylinder 12 is held in loop 18, such that photomask 14 is in contact with photoresist-coated substrate cylinder 12 over a substantial portion of the circumference of substrate cylinder 12, preferably a portion covering greater than about 180 degrees of the surface of substrate cylinder 12 when the substrate cylinder 12 is small. An exposure light device 20 is also provided.

In the embodiment shown in FIGS. 1, 2, and 3, photomask 14 is a continuous band that is directed around drive roller 22, between support rollers 16 to form loop 18, out from support rollers 16, around guide roller 24 and back to drive roller 22. Drive roller 22, support rollers 16 and guide roller 24 are preferably supported parallel to each other by a frame comprising one or more underpinnings (i.e. one or more of various supports known in the art, not shown) in a manner that allows them to freely rotate about their axes.

A tension device, tensions photomask 14 so that photomask 14 is pulled firmly against the surface of substrate cylinder 12. In the embodiment shown in FIGS. 1, 2 and 3, tension is provided by weight roller 26. FIG. 2 shows cylindrical photolithography apparatus 10 when tension is released. FIG. 3 shows cylindrical photolithography apparatus 10 wherein photomask 14 is tensioned. Cylindrical photolithography apparatus 10 further comprises a standard drive mechanism, such as drive roller 22 and drive motor 28 operatively connected by drive belt 30, for moving photomask 14 and thereby rotating substrate cylinder 12 in that photomask 14 also serves as a drive belt that turns the cylinders as shown by the arrows in FIG. 1.

Support rollers 16 must be sufficiently rigid to support substrate cylinder 12 without bending in a manner that could distort photomask 14. Support rollers 16 may have a thin pliable coating to distribute the weight of large substrate cylinders over a wide area to prevent damage to photomask 14. The diameter of support rollers 16 is not critical, provided support rollers 16 are sufficiently rigid to support the length and weight of substrate cylinder 12. For example, support rollers 16 used with a 0.06 inch diameter substrate cylinder 12 preferably may be about 0.5 inches in diameter and made of steel. In contrast, support rollers 16 used with a 4 inch diameter substrate cylinder 12 are typically between about 2 and about 4 inches in diameter. Although cylindrically shaped support rollers 16 are shown in the figures and discussed herein, it should be understood that support rollers 16 need not be cylindrically shaped and need not be a single member. Rather, any support member, or members, over which photomask 14 can smoothly move can be employed in the cylindrical photolithography apparatus 10 of the present invention.

Support rollers 16, guide roller 24 and drive roller 22 are preferably parallel and can be made from any rigid material having sufficient strength to moveably support substrate cylinder 12 and guide photomask 14. The surface finish of the rollers should be sufficiently smooth so as not to damage photomask 14. The distance between support rollers 16 is preferably less than the diameter of the substrate cylinder 12 to be exposed. For example, one-half inch diameter support rollers 16 with a 0.010-inch gap between support rollers 16 can be used for a 0.060-inch-diameter substrate cylinder 12.

The support frame supports the rollers and any other elements of the apparatus, and may include support for light device 20. The support frame should be constructed so as not to interfere with side loading and unloading of substrate cylinder 12. The support frame may be made from aluminum, brass, wood, steel, plastic or any similar rigid material with sufficient stability for the particular application. The rollers are supported by the frame with bearings, bushings or the like so that they are free to turn about their axes.

Substrate cylinder 12 may be prepared by applying a liquid photoresist by dip coating, spray coating, roller coating, or any variation of such methods that would be appropriate for the size of the substrate cylinder 12 being coated and the thickness of the resist required. Liquid resist is dried (soft baked) prior to placement of substrate cylinder 12 in cylindrical photolithography apparatus 10. Alternatively, dry film photoresist can be laminated around the circumference of larger diameter substrate cylinders.

As shown in FIGS. 1, 4 and 7, light device 20 provides light rays to expose the photoresist 31 coating substrate cylinder 12. The type of light device 20 required to provide light of the appropriate wavelength and intensity will be readily calculated by one skilled in the art based on the type of photoresist used. For example, many commercially available photoresists require ultraviolet light. Light device 20 will generally contain a shutter (not shown) or other mechanism to turn the light on and off.

FIGS. 4 through 6 depict an alternative embodiment of the drive mechanism, in which drive crank 32 is connected to drive roller 22, for turning drive roller 22 to move photomask 14 through the cylindrical photolithography apparatus 10. (Note that the same numbers are used on similar parts in all figures.) Alternatively, any other standard drive mechanism for moving photomask 14 is consistent with the present invention. For example, the drive mechanism may act directly on support rollers 16 or substrate cylinder 12 to rotate the roller and/or cylinder which in turn drives photomask 14. The alternative embodiments of the drive mechanism generally may be used with any size substrate cylinder 12 or embodiment of the invention.

FIGS. 4 through 6 also depict an alternative embodiment of the tension device wherein photomask 14 has first and second ends, with one end attached to a weight 34 and the second end connected to drive roller 22, as shown in FIG. 4. As with the alternative embodiments of the drive mechanism, the alternative embodiments of the tension mechanism may be used with any embodiment of the present invention. Further, although weights are disclosed in the Figures, it should be understood that springs, pneumatic mechanisms, magnets, solenoids, motors, the hands of the user, or other suitable mechanisms can be used to generate the tension in photomask 14 required for operation. Sufficient force must be applied to draw photomask 14 into contact with the photoresist coating substrate cylinder 12, but the exact amount of tension is not critical. Generally, a one pound weight is adequate for a six inch wide 0.001 inch thick polyestermetal photomask used with a 0.06 inch substrate cylinder. A 20 pound weight can be used on a 24 inch wide 0.007 inch thick polyester film mask drawn over a 4.125 inch substrate cylinder.

As shown in FIGS. 2 and 5, to insert a new substrate cylinder 12 into the apparatus before use, or to remove the substrate cylinder after use, weight roller 26, weight 34 or other tension device is removed or set to release tension in photomask 14. In such untensioned state, loop 18 in photomask 14 can be expanded such that substrate cylinder 12 can be inserted and/or removed. When cylindrical photolithography apparatus 10 is not in use, a dummy cylinder may be inserted into loop 18 to maintain loop 18. As shown in FIGS. 3 and 6, when cylindrical photolithography apparatus 10 is in use, weight roller 26 or weight 34 is hung on photomask 10 or another tension device is operably engaged to place tension on photomask 14 such that loop 18 is positioned around substrate cylinder 12 and is in contact with the exterior of substrate cylinder 12 over a substantial portion of the circumference of substrate cylinder 12.

The cylindrical photolithography apparatus 10 of the present invention holds photomask 14 in intimate contact with resist-coated substrate cylinder 12 so that the only space between the actual surface of substrate cylinder 12 and photomask 14 results from the thickness of the photoresist, in that the photoresist holds photomask 14 a distance above the actual surface of substrate cylinder 12. Preferably, the patterned side of photomask 14 is placed against the photoresist coating the surface of substrate cylinder 12 to prevent the thickness of photomask 14 from adding to the space. Thus, cylindrical photolithography apparatus 10 minimizes the space that can cause undercutting of the photomask by exposure light. In many applications, the thickness of the resist is small compared to the pattern features needed to be resolved in the photoresist coating the substrate cylinder 12, and the contact printing performed by the cylindrical photolithography apparatus 10 shown in FIGS. 1 through 3 reduces undercutting caused by nonradial light to an acceptable level. This is particularly true for large substrate cylinders 12.

For small substrate cylinders 12 and/or substrate cylinders with a thick resist coating, contact printing alone may not produce a high resolution due to light undercutting photomask 14 in areas of the substrate cylinder 12 removed from the line on the surface of substrate cylinder 12 closest to perpendicular rays from light device 20. In the embodiment of the present invention configured for such substrate cylinders 12, shown in FIGS. 4 through 7, cylindrical lens 36 is provided to produce radial light, perpendicular to the surface of substrate cylinder 12, over the exposure area, as best shown in FIG. 7. Such radial light virtually eliminates undercutting and produces excellent resolution of the pattern. Radial light is equivalent to the collimated light used with conventional flat photolithography. Further, cylindrical lens 36 concentrates the light from light device 20 by collecting light over an area much larger than the area of light projected onto substrate cylinder 12. Thus, use of cylindrical lens 36 not only improves resolution, but also significantly reduces exposure time by focusing light onto substrate cylinder 12. Although a cylindrical lens 36 is shown in the figures and discussed herein, it should be understood that any lens or group of lens elements supported between light device 20 and substrate cylinder 12 that will focus light onto substrate cylinder 12 is consistent with the present invention.

Cylindrical lens 36 is supported above support rollers 16, parallel to substrate cylinder 12 and in line with light device 20 at a distance from substrate cylinder 12 such that the light is focused on the longitudinal axis of substrate cylinder 12. Any lens transparent to the exposure light that will focus the exposure light is consistent with the present invention. For example, a quartz rod 0.4 inches in diameter can be used as cylindrical lens 36 for a 0.06-inch diameter substrate cylinder. Ideally, a cylindrical lens 36 having a focal length f will provide radial light to the surface of substrate cylinder 12 if the center line of cylindrical lens 36 is located a distance d from the center line of substrate cylinder 12. Focal length f can be calculated using the thick-lens equation, as will be readily understood by those skilled in the art. For a cylindrical lens having radius R and refractive index n the thick lens equation is $f=nR/(2(n-1))$.

A convenient method for holding cylindrical lens 36 at the appropriate distance from substrate cylinder 12 employs spacer bands 38 that encircle the circumference of cylindrical lens 36 and rest in operable contact against support rollers 16, such that rotation of support rollers 16 causes rotation of cylindrical lens 36. Preferably, spacer bands 38 are positioned on both ends of cylindrical lens 36, as shown in FIGS. 4 and 7. Spacer bands 38 are constructed of a thickness that will place cylindrical lens 36 at the appropriate distance above substrate cylinder 12. When spacer bands 38 are employed, parallel alignment of cylindrical lens 36 with substrate cylinder 12 is automatic and cylindrical lens 36 can be easily removed to load or unload substrate cylinder 12. Other forms of mechanical support to hold cylindrical lens 36 or other lens at the desired position can also be provided as will be readily understood by one skilled in the relevant art.

Focusing light from light device 20 with cylindrical lens 36 is not perfect. Optical aberration, or in the case of a cylindrical lens, longitudinal aberration, will reduce the precision of the focus. Therefore, in applications requiring extremely high pattern resolution, panel 40 containing slit aperture 42 can be used to restrict light from light device 20 to an area centered on the longitudinal axis of cylindrical lens 36, as shown in FIG. 7. Panel 40 defining slit aperture 42 is placed between light device 20 and cylindrical lens 36 as shown in FIGS. 4 and 7. The width of slit aperture 42 is less than the diameter of cylindrical lens 36. Preferably panel 40 is perpendicular to light rays from exposure device 20.

In general, a narrower slit aperture 42 will result in a sharper and more precise pattern. A narrow slit also will reduce the angular width of the area being exposed on substrate cylinder 12 at any one time and will therefore increase the total time required to expose the entire surface of the substrate cylinder 12. For a particular cylindrical exposure application, the required precision of the image formed in the resist will influence when a narrow slit and long exposure time are required over a wider slit and shorter exposure time.

The following equations can be used to calculate an estimate of the longitudinal aberration for a given slit aperture 42 and cylindrical lens 36. The equations can be used to balance the desire for a sharp focus and pure radial light with the desire to minimize the exposure time. The equations can also guide the selection of material for cylindrical lens 36 and the diameter of cylindrical lens 36 based on geometry that may be fixed by the diameter and position of support rollers 16 and by the diameter of substrate cylinder 12.

Specifically, a measure of the longitudinal aberration S has been derived based on a third-order approximation. The equation for longitudinal aberration, assuming ordinarily parallel light incident on the cylindrical lens 36 of radius R and refractive index n is:

$$S=(n^2h^2RA)/((2(n-1))R^2+nh^2A));$$

where $A=((n-1)/n^4)((3n+2)(n-1)^2+n^3)$, and h is half the width of slit aperture 42.

Figure 8:
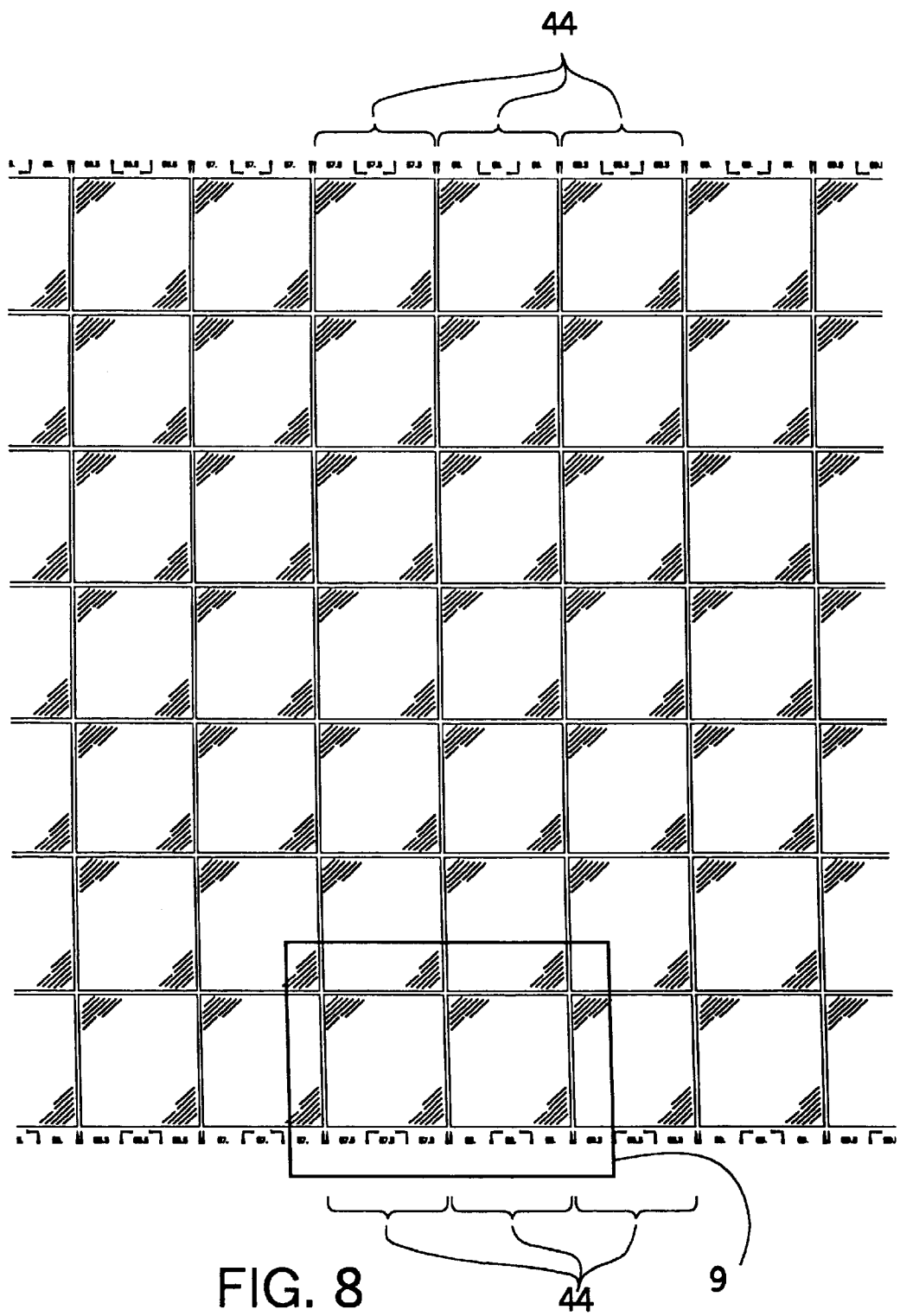
FIG. 8 is a planar view of a section of one embodiment of a photomask for use in the present invention.

FIG. 8 shows detail of a portion of photomask 14 containing patterns 44 to be imaged on the substrate cylinder 12. In applications directed to small end products, for example the coronary stents disclosed in U. S. Pat. application Ser. Nos. 08/819,757 and 09/201,972, the length of substrate cylinder 12 may be many times the length of the stent. In such applications, a single pattern 44 may comprise multiple identical repeating parts to be imaged along the longitudinal axis of substrate cylinder 12, each part corresponding to one complete stent. Substrate cylinder 12 or any intermediate product produced therefrom, may then be cut perpendicular to its longitudinal axis to produce multiple identical stents. In this manner, multiple copies of the stent, or other end product, may be produced from a single substrate cylinder 12.

Figure 9:
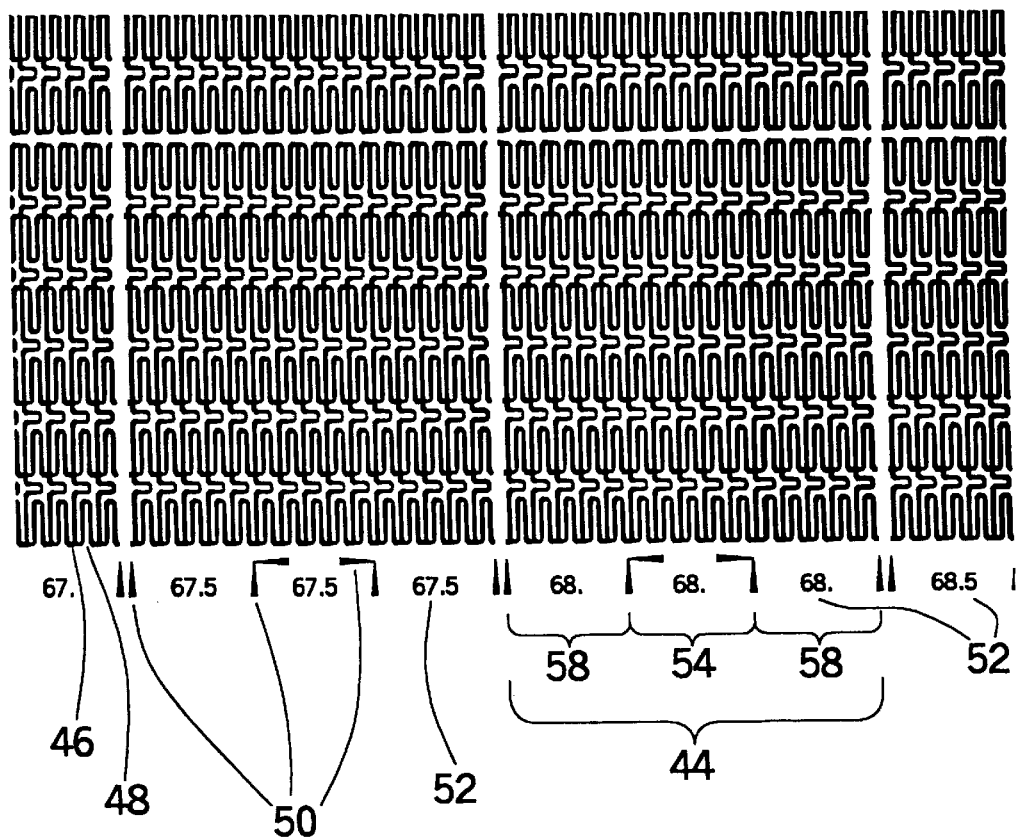
FIG. 9 is a magnified view of box 9 shown in FIG. 8.

As may be better seen in FIG. 9, patterns 44 comprise opaque areas 46 and transparent areas 48. In addition to patterns 44, photomask 14 may include alignment marks 50 and size indicators 52 to assist with selection and positioning of the desired pattern 44. Each pattern 44 may comprise a single primary pattern 54 (not shown) or a pattern set comprised of a primary pattern 54 and repeater patterns 58 as shown in FIG. 9.

In applications in which it is necessary for the pattern on the substrate cylinder to be continuous around the circumference of the substrate cylinder 12, i.e. with no starting or stopping point, the length of primary pattern 54 should be equal to the circumference of substrate cylinder 12. For such applications, size indicators 52 are included to indicate to the user the diameter of the substrate cylinder to which the pattern 44 corresponds. In other applications, for example when primary pattern 54 comprises a page of a book to be exposed onto substrate cylinder 12 for use in printing operations, the pattern will not span the entire circumference of the substrate cylinder, and any substrate cylinder having a circumference somewhat larger than the length of the pattern may be used.

In certain applications requiring a continuous pattern around the circumference of substrate cylinder 12, minor variations between the circumference of the substrate cylinder 12 and the length of primary pattern 54 will create a break in the exposed pattern that is unacceptable for the application. In such applications, a single pattern 44 may be useable only for substrate cylinders with diameters within a very narrow range. To accommodate minor variations in substrate cylinder diameters, photomask 14 may contain several scaled versions of the desired pattern 44 to fit substrate cylinders with varying diameters, as shown in FIG. 9, wherein each pattern version is identical to the other pattern versions except that the length of each pattern 44 is scaled to match a different substrate cylinder diameter. Size indicators 52 reflect the diameter to which each version corresponds. The number of pattern 44 versions on any one photomask 14 is determined by the range of diameters of substrate cylinders 12 used for the application and the variation in diameter that can be adequately covered by a single version of pattern 44. For example, to accommodate substrate cylinders ranging in diameter from 0.066 to 0.072 inches, wherein a single version of pattern 44 will produce adequate 0/360 degree alignment for substrate cylinders 12 having diameters within a 0.0005 inch range, one photomask would have thirteen versions of the same pattern 44 scaled to fit 0.066 to 0.072-inch diameter substrate cylinders in 0.0005-inch increments.

As can be seen in FIGS. 1, 4, and 7, at any one point in time, the light from light device 20 exposes a portion of photoresist 31 coating substrate cylinder 12, not simply a line. In applications in which a continuous pattern will cover the entire circumference of the substrate cylinder, requiring precise alignment at the 0/360 degree point, the primary pattern 54, see FIG. 9, on the photomask 12 is bordered on each side by an identical repeater pattern 58, aligned with primary pattern 54 to create a continuous pattern 44, the length of which is greater than one circumference of the substrate cylinder 12. Thus, if the beginning of primary pattern 54 is positioned at 12 o'clock on the substrate cylinder, when exposure light device 20 is turned on, light strikes a portion of repeater pattern 58 counterclockwise from the beginning of primary pattern 54. Similarly, when substrate cylinder 12 has rotated 360 degrees, light will strike portions of the repeater pattern 58 clockwise from the primary pattern 54. When a small substrate cylinder is used, the pattern 44 preferably comprises three full copies of primary pattern 54, with patterns 44 for larger substrate cylinders generally comprising a primary pattern 54 bordered by repeater patterns 58 comprising only a portion of primary pattern 54. Alignment marks 50 are placed in the margins of the photomask, outside the actual pattern 44, at intervals equal to one complete primary pattern 54 length, the equivalent of one complete substrate cylinder 12 circumference. The second alignment mark 50 in any one pattern 44 comprising a pattern set will generally indicate the beginning of primary pattern 54. Alignment marks 50 are useful for initial positioning of the photomask 14 on the substrate cylinder 12, as further discussed below.

One skilled in the art of photolithography will be familiar with methods to generate or procure flexible film photomasks. As known in the art, photomask 14 will have a first imaged side and a second non-imaged side. Photomask 14 must have sufficient flexibility to bend around the substrate cylinder with no damage to the integrity of the photomask. Generally, for larger substrate cylinders, photomask 14 may be comprised of a standard black and white photographic film negative (for example 0.003-inch or 0.007-inch photographic film), a thin transparent film on which a metallic pattern has been photo lithographically imaged and etched, or any other film consisting of opaque areas 46 and transparent areas 48.

When small diameter substrate cylinders are used, photomasks with sufficient flexibility to bend around the small diameter may not be readily available. When standard photographic film products are too thick, a more flexible mask can be made by depositing an opaque metal coating, (e.g., 500 to 1,000 angstroms of chromium, titanium, aluminum, or the like) on a polyester film or other transparent film sufficiently thin to allow the film to be wrapped around substrate cylinder 12 without damage. Conventional flat contact photolithography can be used to form the desired pattern on the thin flexible photomask 14. This photolithography process can produce opaque patterns on 0.0005-inch-thick films that can be used to image 0.02-inch-diameter substrate cylinders. A photomask 14 formed on about 0.001 to about 0.0015-inch thick polyester is preferable for use with substrate cylinders approximately 0.060-inch in diameter. Thinner masks would be required for small substrate cylinders.

The pattern to be formed on photomask 14 will be determined by the application, the type of resist used, and should be right-reading when the emulsion or metal (i.e., the imaged side) is on the far side of photomask 14, against the photoresist-coated substrate cylinder, as can be readily determined by one skilled in the art. Preferably the pattern will be created by computer design programs. As well-known in the art, computer-generated designs can be plotted on photographic film using a laser pattern generator or other plotters or systems, and computer printers capable of printing on transparency film can be used in some applications. The resolution required by the particular application will influence the method and materials used to produce the mask, as will be readily apparent to one skilled in the art.

A single photomask 14 may contain many patterns 44 of various sizes and/or many different patterns. Additionally, multiple photomasks can be taped together or otherwise connected end-to-end to form a single long photomask 14. A photomask 14 comprising a variety of patterns may be spooled onto drive roller 22 for storage. After a first pattern is exposed onto a first substrate cylinder 12, a new pattern can quickly be brought into position for use on a new job without need to retbread cylindrical exposure apparatus 10. Leader material can also be connected to photomask 14 if additional length is needed to thread cylindrical exposure apparatus 10.

The cylindrical photolithography apparatus 10 described above is used to perform precision contact photolithography directly onto the photoresist-coated surface of substrate cylinder 12. Use of the apparatus generally proceeds as follows: Flexible photomask 14 is positioned in contact with resist-coated substrate cylinder 12 and a tension device applies tension to photomask 14 to pull photomask 14 in contact with substrate cylinder 12 over a substantial portion of the circumference of substrate cylinder 12. The drive mechanism moves photomask 14 so as to rotate substrate cylinder 12 and light from light device 20 is provided to expose pattern 44 onto substrate cylinder 12 over a limited portion of substrate cylinder 12 in contact with photomask 14. Preferably, photomask 14 has a first imaged side and a second non-imaged side and loop 18 is formed such that the imaged side forms the interior surface of loop 18.

In one embodiment of such process, the tension device comprises two weights that are attached to first and second ends of photomask 14 to pull photomask 14 in contact with substrate cylinder 12 over the upper one-half of the circumference of substrate cylinder 12. Alternatively, a portion of photomask 14 forming loop 18 is extended between support rollers 16 and substrate cylinder 12 is placed within loop 18 before substrate cylinder 12 is placed into contact with photomask 14. In one such embodiment, substrate cylinder 12 is supported above support rollers 16, preferably by support rollers 16. In another such embodiment, substrate cylinder 12 is supported below support rollers 16 and is supported by photomask 14. The exposure light device 20 is positioned so that photomask 14 is between light device 20 and substrate cylinder 12.

The above process is more specifically performed as follows: Firstly, the tension device, such as weight 34 or weight roller 26, is removed to release tension on photomask 14. As shown in FIGS. 2 and 5, loop 18 is expanded to allow removal of prior substrate cylinder 12 or the dummy cylinder. The appropriate unexposed substrate cylinder 12 is placed into loop 18, and tension is replaced to pull photomask 14 into contact with substrate cylinder 12, as shown in FIGS. 3 and 6.

When substrate cylinder 12 will be used in an application requiring the pattern to be precisely aligned at the 0 and 360 degree points on substrate cylinder 12, and when photomask 14 contains a variety of patterns 44 in incrementally scaled versions, as shown in FIG. 9, the exact diameter of photoresist-coated substrate cylinder 12 is measured. Photomask 14 is moved through cylindrical photolithography apparatus 10 until the size indicator 52 corresponding to the appropriate version of pattern 44 is in view over substrate cylinder 12. A magnification device may be necessary to read the mask size indicators 52.

After positioning the appropriate incremental version of the pattern, the match of the substrate cylinder 12 to that version of the pattern should be tested in applications requiring a very precise match between substrate cylinder 12 and the pattern length. One method of performing such test comprises releasing the photomask tension and using a small needle point to scratch a mark in the photoresist along the edge of substrate cylinder 12 under one of the alignment marks 50 of photomask 14. Photomask 14 is retensioned and moved a distance equal to one pattern length as indicated by the alignment marks 50 in the margin of the photomask. Magnification may be required to view the alignment marks 50. Movement of tensioned photomask 14 will also drive the rotation of substrate cylinder 12. If the next alignment mark 50 is positioned directly above the scratch made in the photoresist, the version of the pattern on photomask 14 exactly matches the circumference of substrate cylinder 12. If the scratch is counterclockwise of the alignment mark, a smaller version of the mask pattern should be tested. If the scratch is clockwise from the next alignment mark, a larger version of the mask pattern should be used. Alternatively, the test can be performed by an automated means and/or can employ superimposed video images of the position and movement of photomask 14 and substrate cylinder 12.

If a better match between photoresist-coated substrate cylinder 12 and the photomask pattern is required than can be obtained with the incrementally scaled versions of the pattern on photomask 14, photomask 14 can be stretched to obtain a more perfect match. If tension on photomask 14 is supplied by a pneumatic mechanism, increasing the pneumatic tension in photomask 14 can be used to stretch photomask 14, within its elastic limit, to obtain the best possible match. Because the amount of stretch required to make a perfect match is minimal, the integrity of the pattern to be imaged will not be significantly impaired and the integrity of photomask 14 will be maintained for subsequent uses.

When the correct version of the photomask pattern has been selected, photomask 14 must then be placed in the appropriate position over substrate cylinder 12. For patterns 44 comprising a primary pattern 54 bordered by repeater patterns 58, as shown in FIG. 9, photomask 14 is positioned such that the alignment mark 50 at the beginning of the primary pattern 54 is visible over substrate cylinder 12. When the pattern comprises only one copy of the primary pattern 54, such as where the pattern will cover only a portion of the circumference of substrate cylinder 12, the first edge of the pattern should be in view over substrate cylinder 12.

The pattern on photomask 14 is then exposed onto the photoresist coating the exterior of substrate cylinder 12 by activating exposure light device 20 and the drive mechanism. When the drive mechanism is activated to move photomask 14, photomask 14 serves as a drive belt such that when drive roller 22 is turned by the drive mechanism, all other rollers and substrate cylinder 12 revolve. To print an image around the full 360 degree circumference of substrate cylinder 12, photomask 14 must move a distance equal to the circumference of the substrate cylinder 12, which causes substrate cylinder 12 to turn one complete revolution. The novel use of photomask 14 as the drive belt ensures that the surface of substrate cylinder 12 and photomask 14 move at the same speed with no relative motion. Thus, cylindrical photolithography apparatus 10 of the present invention produces a contact print onto the photoresist coating the surface of cylindrical substrate 12. Further, by matching the length of the pattern on photomask 14 to the circumference of the resist coated substrate cylinder 12, as described above, the pattern exposed on substrate cylinder 12 may be continuous, having no definite starting or ending point or break in the pattern.

In the cylindrical photolithography apparatus 10 of the present invention, the area of substrate cylinder 12 exposed at any one point in time is not limited to a narrow area as is the case with the prior methods. Instead, in most applications, about 15 to 50 percent of the exterior surface of the resist coated substrate cylinder 12 is exposed at any one point during the exposure cycle. Exposure takes place while photomask 14 preferably is moved at uniform speed between first and second alignment marks 50 defining primary pattern 54 in the margin of photomask 14, thereby turning the substrate cylinder one revolution. By varying the speed at which photomask 14 is moved through the apparatus, the exposure energy can be varied. For example, changing the speed from one full pattern per minute to one full pattern in two minutes would double the exposure energy. It will be obvious to one skilled in the photolithography and automation arts that various optical and/or video alignment aids and various mechanical systems can be used to control rotation speeds and exposure times.

When the entire circumference of substrate cylinder 12 has been exposed, light device 20 is turned off. A shutter mechanism can be used to turn on and turn off the exposure light. The shutter may be triggered automatically or manually, as will be readily understood by one skilled in the art.

Exposed substrate cylinder 12 is then removed from the cylindrical photolithography apparatus by releasing the tension mechanism to relieve the tension in photomask 14. Loop 18 is gently expanded to allow the exposed substrate cylinder 12 to be removed from the apparatus. The next unexposed substrate cylinder 12, or a dummy cylinder to maintain loop 18, is then inserted into loop 18 and photomask 14 is retensioned as described above.

In a second embodiment of the cylindrical photolithography apparatus 10 of the present invention, as shown in FIGS. 4 through 7, the method for using cylindrical photolithography apparatus 10 includes placing and removing cylindrical lens 36 and/or panel 40 defining slit aperture 42. In such embodiment, before releasing the tension in photomask 14, panel 40 and/or cylindrical lens 36 are removed from the apparatus. Panel 40 and/or cylindrical lens 36 are repositioned after photomask 14 has been retensioned. Cylindrical lens 36 with spacer bands 38 may be placed directly above substrate cylinder 12 to rest upon support rollers 16 such that cylindrical lens 36 will rotate as shown by the arrow in FIG. 4 when photomask 14 is moved by the drive mechanism.

The cylindrical photolithography apparatus of the present invention can be used with a wide variety of substrate cylinders 12 for a wide variety of applications, as will be readily recognized by one skilled in the relevant art. A cylindrical photolithography apparatus consistent with the present invention can accommodate a wide range of substrate cylinder diameters and an unlimited array of patterns on photomask 14. Further, any one cylindrical photolithography apparatus can be scaled to image very small or very large substrate cylinders. Substrate cylinder 12 can generally be any cylinder coated with a photoresist. As will be readily understood by one skilled in the photolithography arts, the substrate cylinders 12 need not be solid and can take the form of tubes or cylindrical sleeves, depending on the application.

In one embodiment of the invention, the cylindrical photolithography apparatus 10 is used to pattern photoresist onto a wire mandrel that is used to electroform cardiovascular stents, as further described in co-pending U.S. Pat. application Ser. No. 08/819,757 and 08/201,972. Alternatively, the cylindrical photolithography apparatus 10 of the present invention can be used to pattern coatings on the surface of optical fibers for various electrical, optical or mechanical purposes. In yet another embodiment of the invention, utilizing larger substrate cylinders 12, the cylindrical exposure apparatus 10 is used to form a pattern on rollers used in printing, engraving or embossing of text or patterns on paper, foil, or fabric.

In a further embodiment of the invention, the cylindrical photolithography apparatus 10 of the present invention can be used to produce cylindrical holographic films that can be used to generate 3-dimensional holographic images that can be viewed from any angle. In such application, a flexible holographic film negative is used as a photomask to expose a pattern in the photoresist on substrate cylinder 10. The shades of gray in the holographic film are converted to depth variations in the photoresist coating substrate cylinder 12 after development. A thin metal coating deposited over the resist, with proper illumination, will diffract light and form a holographic image that can be viewed from any angle around substrate cylinder 12. When the resulting cylinder is turned about its axis, the holographic image also revolves. A cylindrical hologram produced on a transparent substrate cylinder 12 produces a holographic image that can be viewed from the inside of the cylinder looking outwardly.

The foregoing embodiments have been described for illustrative purposes only. Numerous changes, modifications, and alternatives will be contemplated by those skilled in the art without departing from the spirit and scope of the invention. The scope of this invention is limited only by the claims that follow and any modifications within the scope of the claims.

I claim:

1. A cylindrical photolithography apparatus for exposing a pattern contained on a flexible photomask onto a photoresist-coated cylinder, comprising:

at least two adjacent, cylindrical, parallel, rotary support members positioned to receive a portion of the flexible photomask therebetween presenting a loop in the photomask which receives and contacts the photoresist-coated surface of the cylinder, said rotary members rotatably supporting the cylinder with the loop portion of the photomask looped over and engaging the cylinder, said cylinder and the rotary members being simultaneously rotated in response to movement of the photomask;

a drive mechanism operable to move the photomask and provide rotation to the cylinder while the latter is supported by the rotary members;

at least one underpinning on which said support members and drive mechanism are mounted; and at least one light source positioned to direct light of an appropriate wave length and intensity against the photomask looped around the cylinder to expose a portion of the photoresist on the cylinder.

2. The cylindrical photolithography apparatus as claimed in claim 1, wherein is provided a tension device to tension the photomask such that the photomask is pulled against the surface of the cylinder.

3. The cylindrical photolithography apparatus as claimed in claim 1, wherein said tensioning device is selected from the group consisting of weights, pneumatic mechanisms, springs, magnets, solenoids, and motors.

4. The cylindrical photolithography apparatus as claimed in claim 1, further comprising a lens for focusing light on the cylinder, wherein said lens is mounted above said support members, such that the cylinder may be supported between said support members and said lens.

5. The cylindrical photolithography apparatus as claimed in claim 4, wherein said lens is cylindrically shaped.

6. The cylindrical photolithography apparatus as claimed in claim 5, further comprising spacer bands that encircle the circumference of said lens, and wherein said spacer bands support said lens.

7. The cylindrical photolithography apparatus as claimed in claim 4, further comprising a light device positioned above said lens.

8. The cylindrical photolithography apparatus as claimed in claim 7, further comprising a panel defining a slit aperture positioned between said lens and said light device.

9. The cylindrical photolithography apparatus as claimed in claim 2 wherein said drive mechanism comprises a drive crank connected to a drive roller.

10. The cylindrical photolithography apparatus as claimed in claim 2 wherein said drive mechanism comprises a drive motor and drive roller operatively connected by a drive belt.

11. The cylindrical photolithography apparatus as claimed in claim 1 further comprising a moveable flexible photomask wherein a portion of said photomask is received between said support members to form a loop configured to receive the cylinder.

12. The cylindrical photolithography apparatus as claimed in claim 11 wherein said drive mechanism comprises a drive roller parallel to said support members.

13. The cylindrical photolithography apparatus as claimed in claim 12 further comprising a guide roller parallel to said support members and configured to moveably support said photomask.

14. The cylindrical photolithography apparatus as claimed in claim 11 wherein said photomask has a first imaged side and a second non-imaged side and wherein said photomask is configured such that said first imaged side is the interior surface of said loop.

15. A process for exposing a pattern onto a photoresist-coated cylinder, comprising:

providing at least two adjacent, cylindrical, parallel rotary support members;

configuring the flexible photomask to present a loop in contact with the photoresist-coated cylinder;

positioning the cylinder within the loop of the flexible photomask in a location in which the cylinder is supported by the rotary support members to cause the cylinder to be rotated with and in response to rotation of the rotary members;

moving said photomask so as to rotate said rotary support members and said cylinder therewith; and providing at least one light source operable to direct light of an appropriate wave length and intensity against the photomask looped around the cylinder to expose a portion of the photoresist on the cylinder.

16. The process for exposing a pattern as claimed in claim 15, wherein is included the step of applying tension to said photomask to pull said flexible photomask into conforming contact with a substantial portion of the outer circumferential surface of the cylinder.

17. The process for exposing a pattern as claimed in claim 15, wherein is included the step of positioning the rotary support rollers in disposition such that the space between the support rollers is less than the diameter of the cylinder.

18. The cylindrical photolithography apparatus as claimed in claim 1, wherein the space between said rotary support members is less than the diameter of the cylinder.

19. The process for exposing a pattern as claimed in claim 16 wherein said applying tension step comprises attaching weights to first and second ends of said photomask such that said photomask is in contact with said cylinder over the upper one-half of the circumference of said cylinder.

20. The process for exposing a pattern as claimed in claim 15, wherein said cylinder is supported above said support members.

21. The process for exposing a pattern as claimed in claim 15, wherein said cylinder is supported below said support members by said photomask.

22. The process for exposing a pattern as claimed in claim 15, wherein said photomask has a first imaged side and a second non-imaged side and wherein said loop is formed such that said first imaged side is the interior surface of said loop.

* * * * *